United States Patent
Hancock et al.

(10) Patent No.: US 7,300,408 B2
(45) Date of Patent: Nov. 27, 2007

(54) SPECTROSCOPIC BREATH ANALYSIS

(75) Inventors: Graham Hancock, Oxford (GB); Robert Peverall, Oxford (GB); Grant Andrew Dedman Ritchie, Oxford (GB)

(73) Assignee: Isis Innovation Limited, Summertown, Oxford (GB)

( * ) Notice: Subject to any disclaimer, the term of this patent is extended or adjusted under 35 U.S.C. 154(b) by 0 days.

(21) Appl. No.: 10/486,675

(22) PCT Filed: Aug. 16, 2002

(86) PCT No.: PCT/GB02/03826

§ 371 (c)(1), (2), (4) Date: Feb. 12, 2004

(87) PCT Pub. No.: WO03/015631

PCT Pub. Date: Feb. 27, 2003

(65) Prior Publication Data

US 2004/0211905 A1    Oct. 28, 2004

(30) Foreign Application Priority Data

Aug. 16, 2001    (GB) .................................. 0120027.8

(51) Int. Cl.
*G01N 33/497*    (2006.01)
*A61B 5/08*    (2006.01)

(52) U.S. Cl. .................. 600/532; 600/529; 73/23.3
(58) Field of Classification Search .................. 73/23.3; 600/532
See application file for complete search history.

(56) References Cited

U.S. PATENT DOCUMENTS

| | | | |
|---|---|---|---|
| 3,562,524 A | 2/1971 | Moore et al. | |
| 4,468,714 A * | 8/1984 | Russell | 361/62 |
| 4,800,886 A * | 1/1989 | Nestor | 600/311 |
| 5,146,294 A | 9/1992 | Grisar et al. | |
| 5,317,156 A * | 5/1994 | Cooper et al. | 250/345 |
| 5,349,954 A * | 9/1994 | Tiemann et al. | 600/342 |
| 5,515,859 A * | 5/1996 | Paz | 250/339.13 |
| 5,570,697 A * | 11/1996 | Walker et al. | 600/532 |
| 5,625,189 A | 4/1997 | McCaul et al. | |
| 5,929,442 A * | 7/1999 | Higashi | 250/339.13 |
| 5,964,712 A * | 10/1999 | Kubo et al. | 600/529 |

(Continued)

FOREIGN PATENT DOCUMENTS

| | | |
|---|---|---|
| WO | WO 90/00732 | 1/1990 |
| WO | WO 93/15391 | 8/1993 |
| WO | WO 97/49983 | 12/1997 |

(Continued)

OTHER PUBLICATIONS

International Preliminary Examination Report of PCT/GB 02/03826, filed Aug. 16, 2002.
"The C-urea breath test for non-invasive diagnosis of *Helicobacter pylori* infection: which procedure and which measuring equipment?", by F. Parente and G. Bianchi Porro, 2001 Lippincott Williams & Wilkins, pp. 803-806.

*Primary Examiner*—Charles A. Marmor, II
*Assistant Examiner*—Patricia C Mallari
(74) *Attorney, Agent, or Firm*—Westman, Champlin & Kelly, P.A.

(57) ABSTRACT

Methods and apparatus for the analysis of exhaled breath by spectroscopy are disclosed. An optical cavity containing the exhaled breath, typically comprising a pair of opposing high reflectivity mirrors, is used to implement a cavity enhanced absorbtion technique. Pairs of $^{12}CO_2$ and $^{13}CO_2$ absorbtion lines suitable for use in spectroscopic breath analysis are also disclosed.

20 Claims, 3 Drawing Sheets

U.S. PATENT DOCUMENTS

| | | | |
|---|---|---|---|
| 6,148,658 A * | 11/2000 | Chou | 73/24.01 |
| 6,468,222 B1 * | 10/2002 | Mault et al. | 600/531 |
| 6,512,577 B1 * | 1/2003 | Ozanich | 356/73 |
| 6,795,190 B1 | 9/2004 | Paul et al. | 356/437 |

FOREIGN PATENT DOCUMENTS

| | | |
|---|---|---|
| WO | WO 99/61895 | 12/1999 |
| WO | WO 01/13091 | 2/2001 |

* cited by examiner

SPECTROSCOPIC BREATH ANALYSIS

CROSS-REFERENCE TO RELATED APPLICATION

This Application is a Section 371 National Stage Application of International Application No. PCT/GB02/03826, filed 16 Aug. 2002 and published as WO 03/015631 on Feb. 27, 2003.

FIELD OF INVENTION

The present invention relates to apparatus for analysis of exhaled air by spectroscopy, and to methods of operation and uses of such apparatus. Particular embodiments of the invention may be used, for example, to measure the amount of volatile organic compounds present in human breath. Other embodiments may be used to measure $\delta^{13}C$ in exhaled breath pursuant to the $^{13}C$ urea breath test.

BACKGROUND OF THE INVENTION

Human and animal breath contains hundreds of different trace volatile organic compounds (VOCs), in addition to the usual large amounts of $H_2O$ and $CO_2$. The metabolic pathways leading to the generation of these VOCs are mostly little understood. However, much effort has been recently expended correlating the presence of particular VOCs with particular diseases, and breath analysis may yet prove to be a useful and routine procedure for assisting clinicians.

A clinical procedure which currently makes use of breath analysis is the $\delta^{13}C$ urea breath test. This test can be a helpful tool for clinicians seeking to diagnose the presence of a Helicobacter pylori infection in the human gut, which is commonly associated with gastric ulcers and carcinoma. A patient receives an oral dose of urea having a known enhanced level of the $^{13}C$ isotope. Colonies of Helicobacter pylori, which secrete a urease enzyme, hydrolyse the $[^{13}C]$ urea to $^{13}CO_2$ and ammonia. The $^{13}CO_2$ enters the bloodstream and is subsequently exhaled. "$\delta^{13}C$" is a parts per thousand expression of the enhancement in the relative proportions of $^{13}C$ and $^{12}C$ in a sample over a standard or background level.

A common technique employed in the measurement of $\delta^{13}C$ in exhaled breath is isotope ratio mass spectrometry (IRMS). This technique distinguishes between isotopomers of a molecular species, for example $\delta^{13}CO_2$, by the mass/charge ratio of ions of the species. The technique is limited by the existence of two $CO_2$ isotopomers with an atomic mass of 45, namely $^{13}C^{16}O_2$ and $^{12}C^{16}O^{17}O$, as well as by sample contamination with $^{12}C^{16}O_2H$. Furthermore, the technique generally requires high vacuums, low impurity levels, and expensive and bulky equipment.

A number of spectroscopic methods have been proposed as alternative techniques for determining $\delta^{13}CO_2$. These methods exploit the differences in the distributions of rotational and vibrational energy states between $^{12}CO_2$ molecules. A number of such techniques, including nondispersive and fourier transform infrared techniques are mentioned in "Precision Trace Gas Analysis by FT-IR Spectroscopy. 2. The $^{13}C/^{12}C$ Isotope Ratio of $CO_2$", M. B. Esler et al., Analytical Chemistry 72, No. 1, 2000.

Methods currently used for detecting volatile organic compounds in breath analysis were reviewed by W-H Cheng and W-J Lee in "Technology development in breath microanalysis for clinical diagnosis", JL'ab Clin Med 133, No. 3, 1999. The techniques mentioned include gas chromatography, mass spectrometry, fourier transform and nondispersive infrared spectroscopy, the selected ion flow tube and surface acoustic wave techniques, chemiluminescence and colorimetry.

The techniques mentioned above have various disadvantages, particularly when an inexpensive, compact and robust apparatus for clinical use is sought. Mass spectrometry requires bulky and expensive equipment operating with high vacuums and voltages. Gas chromatography relies on the use of specially prepared separation capillaries, may be slow, and is insensitive to isotopic differences. The various infrared spectroscopic techniques are limited by very low IR absorption rates resulting from low concentrations of the target molecule in small experimental volumes, thereby requiring long experiment duration and expensive detectors and post processing circuitry to yield satisfactory results.

SUMMARY OF THE INVENTION

The present invention seeks to address these and other problems of the related prior art. The present invention provides exhaled breath analysis apparatus for quantifying the presence of one or more target substances in exhaled breath comprising:

a cavity enhanced absorption assembly comprising an optical cavity coupled to an optical source operable to emit radiation and an optical detector configured to generate a signal in response to illumination by said radiation;

a breath collection assembly arranged to pass at least a portion of said exhaled breath into said optical cavity for illumination by said radiation; and a data processor connected to said optical detector and adapted to quantify the presence of said one or more target substances in said optical cavity by the contribution to said signal made by absorption of said radiation by said target substance.

The term "cavity enhanced absorption" is used in this document to refer to techniques whereby the signal available due to spectroscopic absorption by a target substance present in an optical cavity is enhanced through repeated reflection of the radiation within the cavity. The repeated reflection increases many times the effective absorption path length of the substances present within the cavity, so that trace components in gas phase are much more easily detected and their presence quantified.

An optical cavity is usually provided by two optically opposed high reflectivity mirrors (typically greater than 99%), and is characterised in that light within the cavity repeatedly retraces some or all of its optical path, leading to resonance, interference and observable energy density build up. Thus optical cavities are fundamentally different in nature and construction to optical multipass cells which are not resonant and in which careful alignment of mirrors permits a light beam to follow an extended, but well defined path between the entry and exit windows of the cell.

The use of an optical cavity within a cavity enhanced absorption assembly enables an extended optical path length to be achieved within a far more compact and lightweight breath analysis apparatus than could be achieved using an equivalent optical multipass cell. The resulting apparatus is also easier to set up and align.

A number of different cavity enhanced absorption techniques are known in the art. Some of these are discussed in "Cavity Enhanced Absorption of Methods at 1.73 µm" by H. R, Barry et al., Chemical Physics Letters 333 (2001) 285-289. In cavity ringdown techniques an optical resonance is built up in an optical cavity before the optical source, typically a pulsed or intermittently operated continuous wave laser, is turned off. The decay time of the cavity resonance, which depends on both the properties of the cavity and the absorptive properties of gas phase components within it, is then measured.

Instead of using an intermittent source, a continuous wave source may be used and the level of resonance continuously measured. In preferred embodiments of the present invention a tunable laser, or more particularly a tunable continuous wave laser diode source is scanned in frequency, using a frequency controller or sweep generator. By scanning the optical source sufficiently quickly to limit the overlap between the source frequency and each natural cavity mode to a timescale shorter than the ringdown time of the cavity, resonant peaks in the output signal due to natural cavity modes are largely avoided. The optical source and one of the cavity mirrors may also be simultaneously modulated to randomise the occurrence of cavity modes which are then lost when averaging the signal over a number of frequency scans of the source.

Instead of scanning, discrete frequencies could in principle be used, selected to include absorption lines of target substances.

The breath collection assembly may include a mouthpiece, typically with an ambient air inlet valve and an outlet valve although such mouthpieces are often treated as single-use or of limited life, so that they will not necessarily be supplied with the apparatus.

The data processor may typically comprise suitable signal conditioning circuitry coupled to suitable signal processing circuitry adapted to digitise the detector output and to pass it to a digital computer for analysis. Usually with reference to the control of the optical source, for example by a sweep generator, the digital computer may be programmed to apply curve or peak fitting algorithms to the spectral data to quantify the presence of the target substance or substances.

The apparatus may be set up to detect spectroscopic absorption lines of $^{12}CO_2$ and $^{13}CO_2$, for example such lines at 1607.634 nm and 1607.501 nm, or at 1627.431 nm and 1627.334 nm, so that it can be used to measure the $\delta^{13}C$ of a subjects exhaled breath. In this way a compact, economical and reliable apparatus for clinicians carrying out the [$^{13}C$] urea breath test or similar procedures may be provided.

A blind detector, substantially identical to or having substantially the same noise characteristics as the optical detector but isolated from the optical cavity, may be provided as a reference in order to improve the signal to noise ratio. This may be done by modulating the signal input to a lock-in amplifier between the optical detector and the blind detector using a Dicke switch or similar arrangement. The Dicke switch is discussed in Review of Scientific Instruments 17(7) (1946) p268.

The invention also provides a method of quantifying the presence of one or more target substances in breath exhaled by a subject, the method comprising the steps of:

collecting said exhaled breath;

passing at least a portion of said exhaled breath into the optical cavity of a cavity enhanced absorption assembly;

illuminating said exhaled breath in said optical cavity with radiation emitted by an optical source;

generating a signal in response to the illumination by said radiation of an optical detector coupled to said optical cavity; and analysing said signal to quantify therefrom the presence of said one or more target substances in said optical cavity by the contribution to said signal made by absorption of said radiation by said target substances.

The invention also provides the use of cavity enhanced absorption in the quantification of one or more target components of exhaled breath, and the use of cavity enhanced absorption in the detection of human and/or animal disease by quantification of one or more components present in breath exhaled by a human or animal.

The target components may include $^{13}CO_2$, $^{12}CO_2$, and volatile organic compounds associated with disease such as alkanes (associated with lung cancer), pentanes (associated with implant rejection, breast cancer, arthritis, asthma) and formaldehyde (associated with breast cancer).

BRIEF DESCRIPTION OF THE DRAWINGS

Embodiments of the invention will now be described by way of example only, with reference to the drawings, of which.

DETAILED DESCRIPTION OF THE PREFERRED EMBODIMENTS

Figure 1:
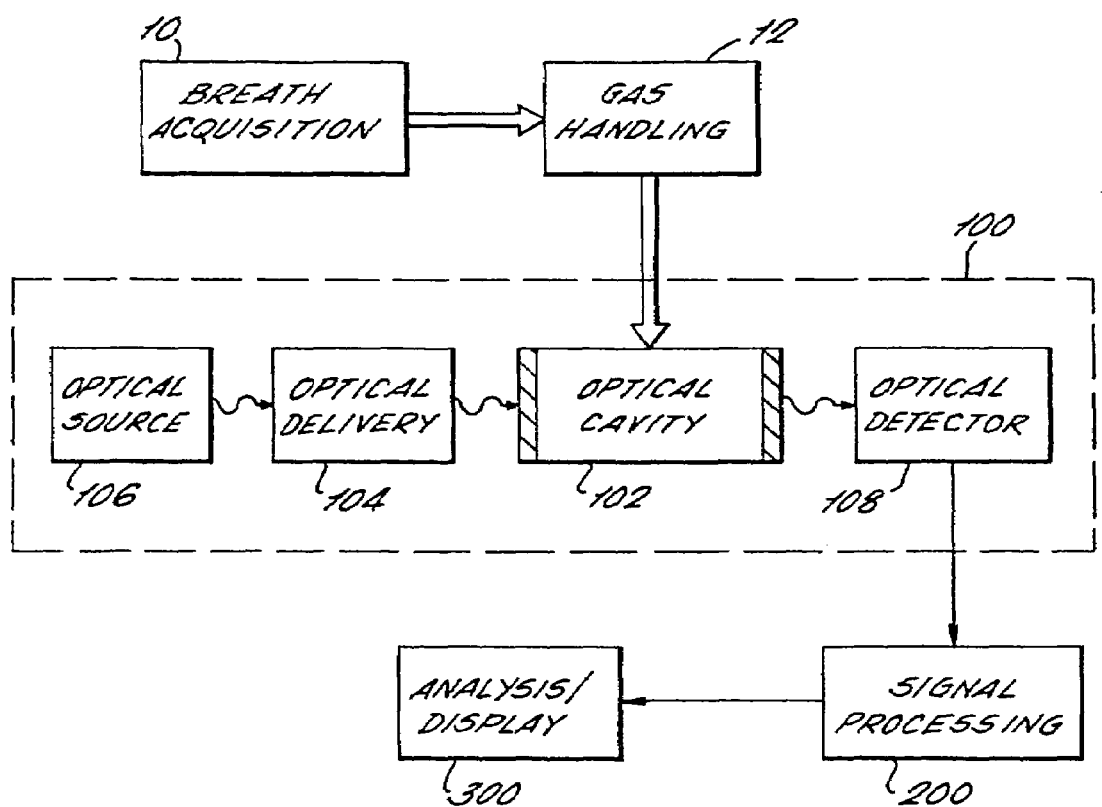
FIG. 1 shows schematically an exhaled breath analysis apparatus embodying the invention.

Referring now to FIG. 1 there is shown schematically an exhaled breath analysis apparatus embodying the present invention. A breath acquisition assembly 10 accepts exhaled breath from a subject. The breath is passed to a gas handling system 12. The gas handling system is arranged to pass required portions of exhaled breath at appropriate pressure, and if required, controlled humidity and/or temperature to the optical cavity 102 of a cavity enhanced absorption (CEA) assembly 100. An optical delivery system 104 feeds electromagnetic radiation generated by an optical source 106 into the optical cavity 102 and an optical detector 108 detects electromagnetic radiation leaving the optical cavity.

The electrical signal from the optical detector 108 is fed to a signal processing arrangement 200, and the resulting data is fed to an analysis/display arrangement 300.

The breath acquisition assembly 10 may typically take the form of a mouthpiece provided with an inlet valve for a subject to draw in environmental or pre-purified air, and an outlet valve to pass exhaled air to the gas handling system 20. The gas handling system may be arranged to sample only alveolar air which has entered sufficiently deeply into the subjects lungs, and not dead-space air from the mouth, oesophagus and broncheoles. The gas handling system may also ensure that exhaled breath passed to the CEA assembly is at an appropriate pressure and falls within particular ranges of temperature and humidity. An apparatus suitable for the collection and handling of exhaled breath prior to spectroscopic analysis, in particular for the detection of volatile organic compounds, is described in "Method for the Collection and Assay of Volatile Organic Compounds in Breath", M Phillips, Analytical Biochemistry 247, 272-278 (1997).

The optical source 106 of the CEA assembly 100 may be provided by a Continuous Wave (CW) laser diode 106, and in particular by a Distributed FeedBack (DFB) laser diode or an extended cavity laser diode. It is important that the optical source remains stable and in single mode operation as it is scanned in frequency across the spectroscopic absorption peaks of gas phase species to be detected. Appropriate optical sources will typically be temperature stabilised, and should be reasonably consistent over their operational lifetime.

The optical source 106 is coupled to the optical cavity 102 by an optical delivery system 104, either directly, or by turning mirrors, optical fibre or both. A Faraday rotator may be used to isolate the optical source from back reflections from the optical cavity 102, especially if a laser diode sensitive to optical feedback is used. The Faraday rotator could be a discrete component or an in-fibre device. Indeed, the entire optical delivery system could be fibre based. Frequency mixing or doubling may be employed to obtain radiation in the desired frequency range.

The optical cavity 102 is constructed from two or more opposed high reflectivity mirrors in a stable geometry, typically separated by a distance of the order of 0.1 to 1.0 m. Mirrors with a reflectivity of about 99.9% are suitable for this application. For a linear geometry cavity with a physical length of 0.5 m the enhanced optical path length due to such mirrors is approximately 500 m. The optical cavity 102 forms part of a vacuum vessel so that samples are not contaminated with environmental air.

Light exiting the cavity through one of the mirrors is detected by the optical detector 108, typically a photo diode, and preferably an InGaAs photodiode sensitive in the infrared.

Light injected into the optical cavity 102 by the optical delivery system 104 undergoes many reflections within the cavity, thus increasing the path length and hence the total absorption by gas species present in the cavity. The optical source 106 is scanned repetitively over the same spectral range to build up a low noise spectrum within the cavity. Light is coupled into the cavity whenever a resonance occurs between a source frequency and a cavity mode. The mode structure of the cavity can be made as congested as possible by mis-aligning the mirrors of the cavity slightly so that many higher order modes can be excited. Coincidences between the frequency of the optical source 106 and the cavity modes can be further randomised by oscillating the cavity length or by superimposing a jitter on the frequency scan of the source.

Preferably, over a single frequency scan of the optical source, several tens of free spectral ranges of the cavity are covered, and many cavity modes are sequentially excited. The time constant of the optical detector 108 can be arranged such that adjacent cavity modes are no longer discretely observed, so that in a single frequency scan a relatively smooth signal is obtained. Hundreds of sequential scans can be averaged together to increase the signal to noise ratio and to let any randomisation processes smooth mode structures which would otherwise be apparent in the data.

Absorption by a target substance in gas phase within the optical cavity 102 is detected by a decrease in the signal output by the optical detector 108. At a particular frequency, the average intensity of the signal is proportional to the ringdown time of the cavity, and thus is inversely proportional to optical losses of the cavity. It is important, when using this technique, that significant radiation fields do not build up inside the cavity. If they do, then rapidly fluctuating output spikes may occur at the optical detector output as cavity modes come into resonance with the optical source, which are detrimental to the smooth output signal otherwise achieved by rapid frequency scanning of the optical source 106.

Figure 2:
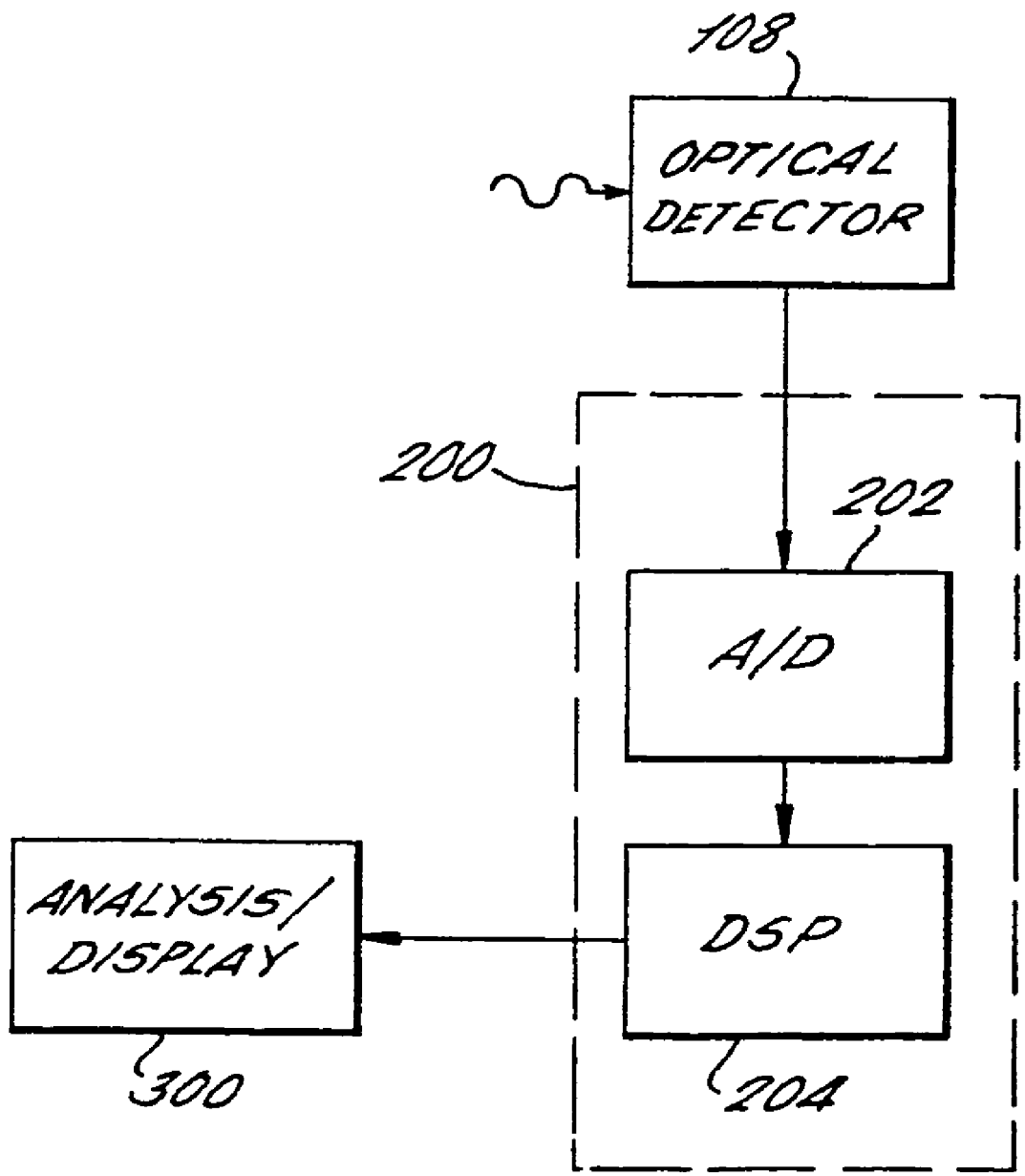
FIG. 2 illustrates signal processing aspects of a first preferred embodiment.

In some embodiments the signal processing arrangement may take the form shown schematically in FIG. 2. The signal from the optical detector, following amplification and other signal conditioning steps if required, is passed to an analogue to digital converter 202 which digitises the optical detector signal and averages over a number of frequency scans of the optical source 106. This averaging and other post processing may be carried out by a digital signal processor 204. The precise specifications of the analogue to digital converter 202 are not critical for the present application. A 10 bit or 12 bit A/D converter should provide sufficient accuracy for the present application. An 8 bit A/D converter is likely to be insufficient. The sampling rates available in such devices far exceed the frequency scan rates likely to be used for the optical source, which may be 20-30 Hz.

If the signal to noise ratio in the optical detector signal is too low for an accurate determination of absorption peak features then several possible means of enhancement are available. A digital signal processor 204 may be used to apply low pass fourier transform filtering or Savitzky-Golay smoothing (which could also be carried out by software in the analysis/display arrangement 300.

The modulation of an optical source is frequently used in optical engineering to improve the signal to noise ratio of a subsequently detected signal. However, in the present application, modulation of the optical source, for example by means of a pre-cavity acoustic optic modulator, tends to alter the way in which cavity resonance builds up in a non-linear manner. A more suitable arrangement is to modulate the detector by switching between it and another device of identical or very similar noise characteristics.

Figure 3:
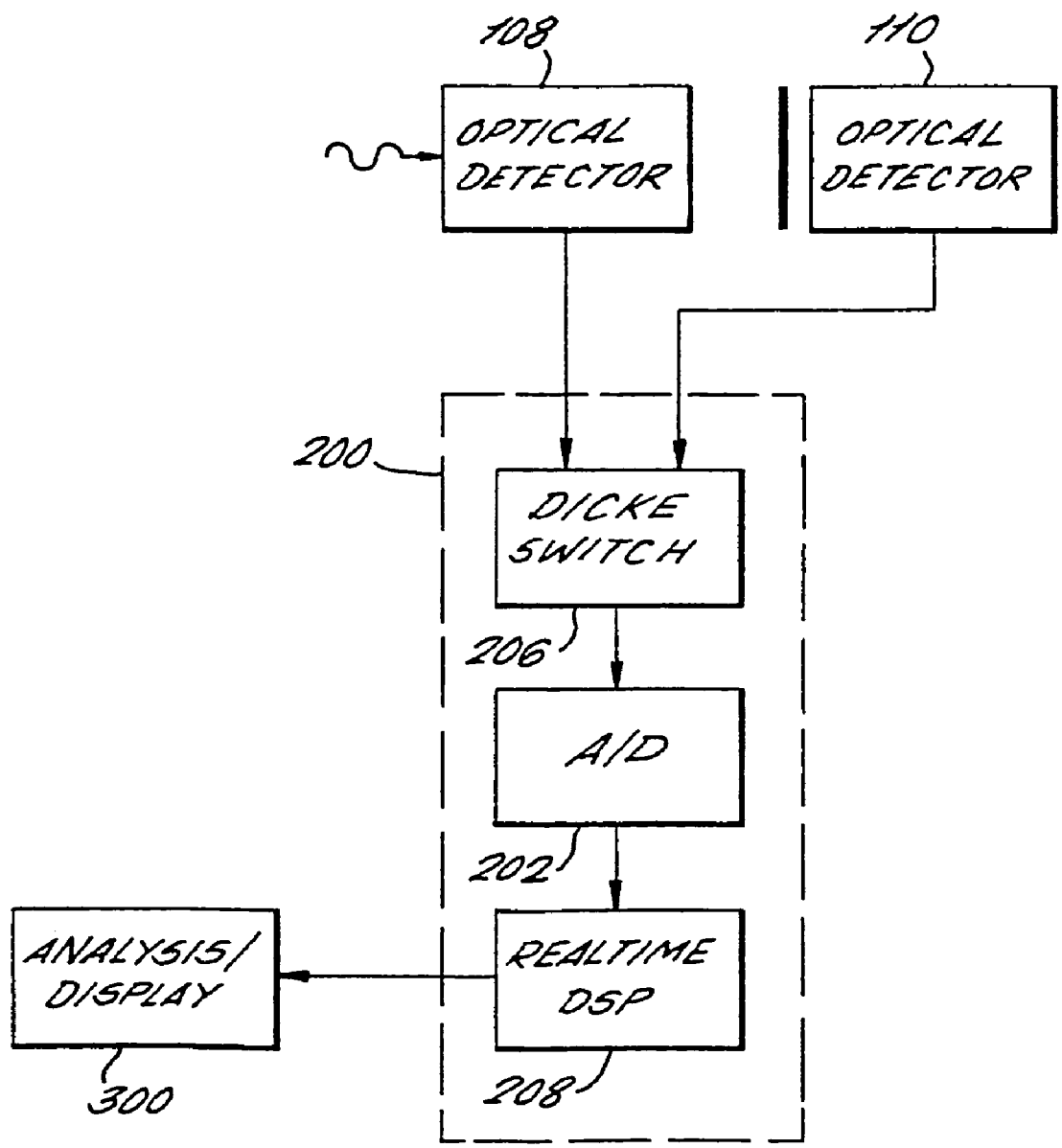
FIG. 3 illustrates signal processing aspects of a second preferred embodiment.

In the lock-in amplifier arrangement of FIG. 3, the detected signal is modulated between the optical detector 108 and an adjacent identical but unilluminated optical detector 100, for example using a Dicke Switch arrangement as discussed in R. H. Dicke, Rev. Sci. Instrum., 17(7) (1946) p268. As well as making good use of the lock-in amplifier made up of an analogue to digital converter 202 and a real-time digital signal processor 208, this technique has the added benefit of rejecting ambient noise in the signal through phase sensitive detection.

The analysis/display arrangement 300 is preferably provided by a suitable digital computer, either as a suitable programmed general purpose personal computer or as a dedicated computer, with suitable input, output and data storage facilities. The output of the signal processing arrangement 200 may be easily communicated to the analysis/display arrangement 300 using methods familiar to the person skilled in the art. Analysis of the output from the signal processing arrangement is preferably carried out using software specifically designed to apply a non-linear curve fitting procedure to the spectral data with baseline, peak frequency and peak shape as fitting parameters.

Specific absorption lines for the determination of concentration of a target species within the optical cavity may be selected using high resolution spectral data, available from the literature or by use of known spectroscopic techniques. Target spectral lines should be selected such that they do not overlap with lines of other, non-target species likely to be present, such as water or methane in the case of analysis of human breath $CO_2$.

If absolute concentration is to be measured then the target absorption line should be chosen to be in close proximity with a reference absorption line of a species of known concentration within the sample. For the analysis of human breath methane is suitable for this purpose, because it is present in the atmosphere at a known concentration close to 1.6 parts per million by volume. Suitably close proximity is within the normal frequency scan range to be used to measure the target absorption line, typically about 1 cm$^{-1}$, but far enough apart for the target and reference lines not to overlap significantly. A calibrated ratio of the measured strength of the target and reference absorption lines then provides the concentration of the target species.

When isotopic ratios are to be measured, a pair of lines should be chosen, one from each isotopomer, based on a maximisation of the following criteria:
(i) the two lines should be in close proximity, as discussed above;
(ii) the two lines should be of similar intensity for a naturally occurring isotopic ratio of the isotopomers;
(iii) the two lines should not be overlapped by other lines originating from the target molecule or by structured absorptions from other sample constituents to a significant or problematic extent;
(iv) the ratio of intensities of the two lines should not vary significantly with temperature over any expected experimental temperature fluctuation. For $CO_2$ absorption, the lines may originate from rotational levels in the ground state of $CO_2$.

A particular configuration and use of the apparatus described above will now be discussed. Helicobacter pylori is one of the most common bacteria found in humans, and its presence has been linked to the incidence of a variety of stomach diseases including gastric ulcers and carcinoma. Colonies of this bacterium in the human stomach can be detected non-invasively by the measurement of isotopic ratios in $CO_2$ in the exhaled breath of patients following ingestion of $^{13}C$ labelled urea.

An exhaled breath analysis apparatus as described above may be constructed or configured to measure the $^{13}C/^{12}C$ ratio by infrared spectroscopy on high overtone absorption bands of $CO_2$ using radiation from a laser diode near 6000 cm$^{-1}$.

The diode laser optical source is scanned over a wavelength range of 0.2 nm which encompasses one absorption line of each of the isotopomers $^{13}CO_2$ and $^{12}CO_2$, for example at 1607.501 nm and 1607.634 nm respectively. The transitions giving rise to these absorption lines are selected so that in a sample of $CO_2$ with a naturally occurring isotopic abundance the two lines have approximately equal absorption intensities.

Other pairs of $^{13}CO_2$, $^{12}CO_2$ lines, in vacuum nanometres, which are also suitable for this purpose are:

| | |
|---|---|
| 1596.978, | 1596.869 |
| 1597.241, | 1597.361 |
| 1597.512, | 1597.361 |
| 1606.997, | 1607.142 |
| 1608.014, | 1608.057 |

The ratio of the two isotopic species may be measured as a function of time following the ingestion of $^{13}C$ labelled urea by a patient suspected of harbouring a *Helicobacter pylori* infection. After ingestion of a standard 100 mg sample of $^{13}C$ urea, a change in $\delta^{13}C$ of +5 after 30 minutes is considered to be a positive test for the bacterium. The apparatus may calibrate against an unelevated $^{13}C$ level using an internal standard or by sampling ambient atmospheric air.

The described apparatus does not generally require a separate reference cell. Wavelength calibration can be accomplished by frequency scanning over a region which encompasses absorption lines of various species, including the target line or lines, and by recognition of the resulting absorption spectrum. For absolute concentrations absorption levels can be compared with those of a species of known concentration which is introduced into the sample, or which is naturally occurring such as methane. For isotopic ratio measurements, the levels of the two isotopomers present in a reference sample, such as exhaled breath before ingestion of $^{13}C$ labelled urea in the case of a $^{13}C/^{12}C$ breath test, can be used as a relative standard, and the apparatus calibration can be checked from time to time with such reference, or preprepared standard samples.

The apparatus may need to operate with a reduced gas pressure in the optical cavity 102 in order to increase selectivity by removing pressure broadening effects. However, such an arrangement, which can be effected by the gas handling system 12, should only have a minor effect upon the instrument sensitivity.

The apparatus may also be used for $CO_2$ isotopic analysis to assist in the measurement of fat digestion in humans, particularly infants, and observing delayed gastric emptying associated with diseases such as diabetes-and aids, and the detection of specific enzymes associated with disease by supplying the enzymes with $^{13}C$ labelled material.

The apparatus may also be used, if suitably constructed or configured, to detect and quantify the presence in exhaled breath of various other compounds including specific volatile organic compounds. The first overtones of vibrational transitions of the C—H bands of such compounds lie conveniently in the wavelength range of commercially available diode lasers. For example, specific alkanes have been detected at elevated levels in the breath of lung cancer patients, in particular methylpentane. Other diseases such as breast cancer, transplant rejection and asthma have been associated with elevated levels of pentanes, and formaldehyde has been observed at elevated levels in breast cancer patients.

The invention may be used in the detection of isotopically specialled water ($H_2O$/HDO), for example in determining human body fluid status within applications such as dialysis treatment. The effectiveness of dialysis treatment could also be monitored by measuring exhaled $NH_3$. Exhaled nitric oxide (NO) could also be measured using the invention, for example in the monitoring of asthma.

The spectroscopic apparatus described herein may be used for a variety of applications other than the analysis of exhaled breath, by providing an appropriate sample collection and/or injection assembly, and by selecting appropriate target absorption lines for detection. Other applications include the detection of explosives and nerve gas, and detecting indications of the proximity of oil and gas deposits through the isotopic makeup of methane present in drilling mud.

The invention claimed is:

1. Exhaled breath analysis apparatus for quantifying the presence of one or more target substances in exhaled breath comprising:
a cavity enhanced absorption assembly comprising an optical cavity coupled to an optical source operable to emit radiation and an optical detector configured to generate a signal representative of the intensity of radiation in said optical cavity, wherein the optical cavity is arranged to allow radiation emitted from the optical source to be repeatedly reflected and retrace its path to excite a plurality of cavity modes;
a breath collection assembly arranged to pass at least a portion of said exhaled breath into said optical cavity for illumination by said radiation; and a data processor connected to said optical detector and adapted to quantify the presence of said one or more target substances in said optical cavity by measuring a reduction in the intensity of radiation in said optical cavity caused by variations in cavity ringdown time caused by absorption of said radiation by said target substance.

2. The apparatus of claim 1 wherein said optical source is a tunable laser.

3. The apparatus of claim 2 further comprising a frequency controller connected to said tunable laser, the frequency controller being configured to cause the optical source to repeatedly change the frequency of said radiation within a predefined range comprising one or more absorption lines of said target substances.

4. The apparatus of claim 3 wherein the frequency controller is a sweep generator adapted to cause the optical source to repeatedly sweep the frequency of said radiation across a predefined range comprising one or more absorption lines of said target substances.

5. The apparatus of claim 3 wherein said absorption lines comprise at least a first line characteristic of $^{12}CO_2$ and at least a second line characteristic of $^{13}CO_2$.

6. The apparatus of claim 5 wherein said first line has a wavelength of about 1607.634 nm and said second line has a wavelength of about 1607.501 mm.

7. The apparatus of claim 1 further comprising a blind detector having substantially the same noise characteristics as said optical detector, said blind detector being optically isolated from said radiation and connected to said data processor.

8. The apparatus of claim 7 wherein said optical detector and said blind detector are connected to said data processor by a Dicke switch, and said data processor comprises a lock-in amplifier.

9. The apparatus of claim 1 wherein the optical cavity comprises at least two opposed mirrors.

10. The apparatus of claim 1 wherein said optical cavity is configured so as to yield an effective path length of said radiation within the optical cavity of at least 10 meters.

11. A method of quantifying the presence of one or more target substances in breath exhaled by a subject, the method comprising the steps of:
collecting said exhaled breath;
passing at least a portion of said exhaled breath into an optical cavity of a cavity enhanced absorption assembly, wherein the optical cavity is arranged to allow radiation emitted from an optical source to be repeatedly reflected and retrace its path to excite a plurality of cavity modes;
illuminating said exhaled breath in said optical cavity with radiation emitted by the optical source;
generating a signal representative of the intensity of radiation in said optical cavity by means of an optical detector coupled to said optical cavity; and
analysing said signal to quantify therefrom the presence of said one or more target substances in said optical cavity by measuring a reduction in the intensity of radiation in said optical cavity caused by variations in cavity ringdown time caused by absorption of said radiation by said target substances.

12. The method of claim 11 further comprising the step of repeatedly changing the frequency of said radiation within a predefined range comprising one or more absorption lines of said target substances.

13. The method of claim 12 wherein the step of repeatedly changing the frequency of said radiation comprises the step of repeatedly sweeping the frequency of said radiation across a predefined range comprising one or more absorption lines of said target substances.

14. The method of claim 12 wherein said absorption lines comprise at least a first line characteristic of $^{12}CO_2$ and at least a second line characteristic of $^{13}CO_2$.

15. The method of claim 14 wherein said first line has a wavelength of about 1607.634 nm and said second line has a wavelength of about 1607.501 mm.

16. The method of claim 11 further comprising the step of generating a reference signal using a blind detector substantially identical to said optical detector, said blind detector being optically isolated from said optical cavity and connected to said data processor, and using said reference signal in said step of analysing.

17. The apparatus of claim 1 wherein the data processor is adapted to determine the absorption of radiation by a breath sample at the wavelengths of a $^{13}CO_2$ absorption line and a $^{12}CO_2$ absorption line selected from the list of ($^{13}CO_2$, $^{12}CO_2$) absorption lines comprising:

| |
|---|
| (1596.978 nm, 1596.869 nm) |
| (1597.241 nm, 1597.361 nm) |
| (1597.512 nm, 1587.361 nm) |
| (1606.997 nm, 1607.142 nm) |
| (1607.501 nm, 1607.634 nm) |
| (1608.014 nm, 1608.057 nm). |

18. The method of claim 11 including quantifying the presence of $^{13}CO_2$ and $^{12}CO_2$ in exhaled breath by determining the absorption of radiation by a breath sample at the wavelengths of a $^{13}CO_2$ absorption line and a $^{12}CO_2$ absorption line selected from the list of ($^{13}CO_2$, $^{12}CO_2$) absorption lines comprising:

| |
|---|
| (1596.978 nm, 1596,869 nm) |
| (1597.241 nm, 1597.361 nm) |
| (1597.512 nm, 1587.361 nm) |
| (1606.997 nm, 1607.142 nm) |
| (1607.501 nm, 1607.634 nm) |
| (1608.014 nm, 1608.057 nm). |

19. A method for using cavity enhanced absorption to quantify one or more target components of exhaled breath the method comprising:
passing at least a portion of said exhaled breath into an optical cavity;
illuminating said exhaled breath in said optical cavity with radiation emitted by an optical source, wherein the optical cavity is arranged to allow radiation emitted from the optical source to be repeatedly reflected and retrace its path to excite a plurality of cavity modes; and
measuring a reduction in the intensity of radiation in said optical cavity caused by variations in cavity ringdown time caused by absorption of said radiation in said optical cavity by said one or more target components of exhaled breath, thereby to quantify said one or more target components of exhaled breath.

20. A method for using cavity enhanced absorption to detect human or animal disease comprising quantifying one or more target components in breath exhaled by a human or animal by the steps of:
passing at least a portion of said exhaled breath into an optical cavity;

illuminating said exhaled breath in said optical cavity with radiation emitted by an optical source, wherein the optical cavity is arranged to allow radiation emitted from the optical source to be repeatedly reflected and retrace its path to excite a plurality of cavity modes;

measuring a reduction in the intensity of radiation in said optical cavity caused by variations in cavity ringdown time caused by absorption of said radiation in said optical cavity by said one or more target components in said breath exhaled; and detecting human or animal disease on the basis of the quantified one or more target components in said breath exhaled.

\* \* \* \* \*